United States Patent [19]

Kondo et al.

[11] Patent Number: 5,587,474
[45] Date of Patent: Dec. 24, 1996

[54] METHOD FOR REMOVING THE PROTECTING GROUP FOR CARBOXYL GROUP

[75] Inventors: Kazuhiko Kondo, Osaka; Hiroshi Horikawa, Kawanishi; Tameo Iwasaki, Nishinomiya, all of Japan

[73] Assignee: Tanabe Seiyaku Co., Ltd., Osaka, Japan

[21] Appl. No.: 77,383

[22] Filed: Jun. 17, 1993

[30] Foreign Application Priority Data

Jun. 18, 1992 [JP] Japan .................................. 4-202866
Dec. 4, 1992 [JP] Japan .................................. 4-325031

[51] Int. Cl.$^6$ ............................................. C07D 403/12
[52] U.S. Cl. .................................................. 540/350
[58] Field of Search ........................................ 540/350

[56] References Cited

U.S. PATENT DOCUMENTS 4,174,316  11/1979  Christensen et al. ................ 260/239

FOREIGN PATENT DOCUMENTS

| 0013663 | 7/1980 | European Pat. Off. . |
| 0160876 | 4/1985 | European Pat. Off. . |
| 0215739 | 5/1986 | European Pat. Off. . |
| 0384732 | 2/1990 | European Pat. Off. . |
| 0410727 | 7/1990 | European Pat. Off. . |
| 0474243 | 9/1991 | European Pat. Off. . |
| 9202521 | 2/1992 | European Pat. Off. . |
| 55-105686 | 8/1980 | Japan . |
| 55-69586 | 9/1980 | Japan . |
| 58-103358 | 6/1983 | Japan . |
| 6058987 | 4/1985 | Japan . |
| 60-202886 | 10/1985 | Japan . |
| 61-5081 | 1/1986 | Japan . |
| 62-277389 | 12/1987 | Japan . |
| 3396 | 1/1991 | Japan . |
| 441489 | of 1992 | Japan . |
| 2176478 | 6/1986 | United Kingdom . |

OTHER PUBLICATIONS

Journal Of Organic Chemistry; Homogenous, Palladium (0)–Catalyzed Exchange Deprotection of Allylic Esters, Carbonates, and Carbamates. 1982, vol. 47 No. 3, pp. 587–590.
Journal Of Organic Chemistry; Cepohalosporin 3'-Quinolone Esters with a Dual Mode of Action. vol. 33, No. 1, pp. 77–86.

Primary Examiner—Mukund J. Shah
Assistant Examiner—King Lit Wong
Attorney, Agent, or Firm—Browdy and Neimark

[57] ABSTRACT

A method for removing substituted or unsubstituted allyl group from β-lactam compound having substituted or unsubstituted allyl group-protecting carboxyl group, which comprises treating said β-lactam compound with palladium catalyst in the presence of allyl-scavenger in aqueous organic solvent, by which the substituted or unsubstituted group can be easily and effectively removed under moderate conditions so that the desired compound can be obtained in high yield at low cost.

16 Claims, No Drawings

METHOD FOR REMOVING THE PROTECTING GROUP FOR CARBOXYL GROUP

The present invention relates to a novel method for removing the protecting group for carboxyl group.

Prior Art

β-Lactam compounds having a carboxyl group have been known to be useful as an antimicrobial agent having excellent antimicrobial activity or a useful intermediate thereof. For instance, there are disclosed various β-lactam antimicrobials such as penem antimicrobials [cf. Japanese Patent Second Publication (Kokoku) No. 396/1991, Japanese Patent First Publication (Kokai) No. 105686/1980, Japanese Patent First Publication (Kokai) No. 58987/1985], carbapenem antimicrobials [cf. Japanese Patent First Publication (Kokai) No. 202886/1985, Japanese Patent First Publication (Kokai) No. 5081/1986, Japanese Patent First Publication (Kokai) No. 233077/1985, Japanese Patent First Publication (Kokai) No. 69586/1980, EP-A-474243], oxapenem antimicrobials [cf. Japanese Patent First Publication (Kokai) No. 103358/1983], cephem antimicrobials [cf. Japanese Patent First Publication (Kokai) No. 277389/1987], carbacephem antimicrobials (cf. U.S. Pat. No. 4,174,316), and the like.

In the processes for preparing these conventional β-lactam antimicrobials, there are used intermediates having a protected carboxyl group, and such protecting groups for carboxyl group are a substituted or unsubstituted allyl group such as allyl group, 3-methylallyl group, 3-phenylallyl group, and the like.

On the other hand, there have been known various methods for removing the above mentioned substituted or unsubstituted allyl groups, for example, 1) treating with tetrakis(triphenylphosphine) palladium (0) in the presence of 2-ethylhexanoic acid potassium salt in a mixture of ethyl acetate/methylene chloride [cf. The Journal of Organic Chemistry, Vol. 47, pp 587–590 (1982)], or 2) treating with palladium diacetate and triethyl phosphite in the presence of 2-ethylhexanonic acid sodium salt in a mixture of ethyl acetate/methylene chloride [cf. Journal of Medicinal Chemistry, Vol. 33, pp. 77–86 (1990)], and the like.

However, in case that above mentioned substituted or unsubstituted allyl group are removed from compounds having an unstable structure such as β-lactam compounds, the above mentioned conventional methods have various defects, for example, the yield of the product is low because the desired compound are decomposed during the reaction, or the removal of the protecting group is not completely accomplished, or the efficiency of catalytic cycle is bad so that a large amount of catalyst is required.

BRIEF DESCRIPTION OF THE INVENTION

An object of the present invention is to provide a novel method for removing the protecting groups for carboxyl group. More particularly, the present invention provides a novel method for removing effectively a substituted or unsubstituted allyl group from a compound having a substituted or unsubstituted allyl group-protecting carboxyl group without decomposition of the desired product, even though the such compound has an unstable structure, such as β-lactam compound.

DETAILED DESCRIPTION OF THE INVENTION

According to the present invention, the removal of the protecting group from a β-lactam compound having a substituted or unsubstituted allyl group-protecting carboxyl group is carried out by treating said β-lactam compound with a palladium catalyst in the presence of an allyl-scavenger in an aqueous organic solvent. The organic solvent in the "aqueous organic solvent" may be any one being able to mix with water which does not disadvantageously affect the reaction, especially a polar organic solvent is more preferable. The polar organic solvent includes, for example, lower alkanols, tetrahydrofuran, dioxane, dimethylformamide, dimethylsulfoxide, acetonitrile, acetone, hexamethylphosphoric triamide (HMPA), and the like. Among these solvents, ethanol, tetrahydrofuran and dioxane are more preferable.

Besides, the content of water in these aqueous organic solvents are preferably in the range of 5%–50%, more preferably in the range of 10%–20%.

The palladium catalyst may be any palladium complex (0), for example, tetrakis(triphenylphosphine)palladium (0), di[1,2-bis(diphenylphosphino)ethane]palladium (0), bis-(dibenzylidenacetone)palladium (0), and the like, and tetrakis(triphenylphosphine)palladium (0) is more preferable.

Besides, instead of using the above mentioned palladium complex (0), it is possible to use a palladium compound (II) and a phosphine compound which react to form a palladium complex (0) in the reaction system. The palladium compound (II) includes, for example, palladium di-lower alkanates (e.g. palladium diacetate) and palladium dihalides (e.g. palladium dichloride), and the phosphine compound includes, for example, tri-lower alkyl phosphites (e.g. trimethyl phosphite, triethyl phosphite), and triphenylphosphine. Particularly, a combination of a palladium di-lower alkanate and a tri-lower alkyl phosphite is preferable.

The allyl-scavenger may be any conventional ones such as ones disclosed in Japanese Patent First Publication (Kokai) No. 79180/1989, for example, alicyclic β-dicarbonyl compounds (e.g. dimedone, 1,3-cyclohexadione), aliphatic β-dicarbonyl compounds (e.g. acetylacetone, ethyl acetoacetate), aromatic amines (e.g. N-lower alkylaniline, aniline), alkanoic acids having 2–9 carbon atoms (e.g. acetic acid, propionic acid, 2-ethylhexanonic acid) and alkali metal salts thereof, and di-lower alkylamines (e.g. dimethylamine, diethylamine). Among these compounds, alicyclic β-dicarbonyl compounds, aliphatic β-dicarbonyl compounds and aromatic amines are more preferable. Besides, said allyl-scavengers may be used not only for removing unsubstituted allyl groups but also for removing substituted allyl groups as well.

The reaction of the present invention can more preferably be carried out by using as an aqueous organic solvent a mixture of ethanol and water, a mixture of tetrahydrofuran and water, or a mixture of dioxane and water, and as a palladium catalyst tetrakis(triphenylphosphine)palladium (0) or a palladium complex (0) obtained by reacting a palladium diacetate and triethyl phosphite in the reaction system, and as an allyl-scavenger dimedone.

The reaction of the present invention can preferably be carried out under cooling, at room temperature or with heating, for example, at a temperature from −30° C. to 100° C., more preferably at a temperature from 20° C. to 40° C.

The reaction of the present invention is preferably carried out in the presence of an inorganic or organic base, and the base includes, for example, alkali metal compounds (e.g. alkali metal hydrogen carbonates, alkali metal carbonates, alkali metal hydroxides, alkali metal hydrides, etc.), organic amines, and the like. These bases are usually used in an amount of 0.1 to 10 equivalents, preferably 1 to 4 equivalents to the starting compound, which is sufficient amount for keeping the pH value of the reaction system at pH 5–9, especially at pH 6–8, so that the β-lactam ring is not cloven.

In the reaction of the present invention, the substituted or unsubstituted allyl group may be groups of the formula: $-CH_2-CH=CHR^0$ (wherein $R^0$ is hydrogen atom, a lower alkyl group or aryl group), more particularly allyl group, 3-methylallyl group, 3-phenylallyl group, and the like.

The β-lactam compound having a substituted or unsubstituted allyl-protecting carboxyl group may be any conventional ones, for example, compounds having a partial structure of the following formula:

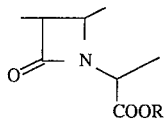

wherein R is a substituted or unsubstituted allyl group, more particularly, compounds of the following formula [I]:

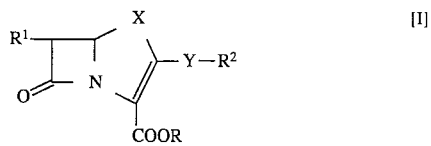

wherein R is a substituted or unsubstituted allyl group, each of $R^1$ and $R^2$ is independently an organic group, X is a group of the formulae: $-CH_2CH_2-$, $-S-CH_2-$, $-O-CH_2-$, $-CH_2-$, $-CH(R^3)-$, $-S-$ or $-O-$, $R^3$ is a lower alkyl group, and Y is sulfur atom, oxygen atom or a single bond. More preferable β-lactam compounds having a substituted or unsubstituted allyl-protecting carboxyl group are compounds of the formula [II]:

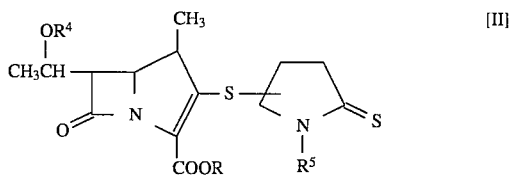

wherein R is a substituted or unsubstituted allyl group, $R^4$ is hydrogen atom or a protecting group for hydroxy group, and $R^5$ is hydrogen atom or a lower alkyl group.

The above mentioned β-lactam compounds are useful as an antimicrobial agent, a prodrug thereof, or a synthetic intermediate thereof.

In the formula [I], the organic group for $R^1$ may be any conventional ones which are used in the conventional β-lactam antimicrobials. Suitable examples of the organic groups are hydrogen atom, amino group, azide group, mercapto group, a lower alkyl group, a lower alkoxy group, a lower alkoxythio group, aryl group (e.g. phenyl, naphthyl, etc.), a carbonyl group substituted by a heterocyclic group (e.g. pyrrolidinyl, piperidyl, furyl, thienyl, imidazolinyl, pyridyl, etc.), a lower alkanoyl group substituted by a heterocyclic group (e.g. pyrrolidinyl, piperidyl, furyl, thienyl, imidazolinyl, pyridyl, etc.). Moreover, these groups may have one or more substituents, and the suitable examples of the substituent are amino group, hydroxy group, a lower alkyl group, a lower alkoxy group, a lower alkanoyl group, a lower alkanoylamino group, a lower alkoxy-lower alkanoyl group, mercapto group, a lower alkylthio group, an aralkyl group, an aralkyloxycarbonyl group, a heterocyclic group (e.g. tetrahydropyranyl, etc.), and a lower alkanoyl group substituted by a heterocyclic group (e.g. thienyl).

The organic groups for $R^2$ may be any conventional ones which are used in the conventional β-lactam antimicrobials as well as $R^1$, and the suitable examples of the organic groups are a lower alkyl group, a cycloalkyl group, an aryl group (e.g. phenyl, etc.), and a heterocyclic group having at least one nitrogen atom, oxygen atom or sulfur atom as a heteroatom (e.g. pyrrolidinyl, piperidyl, furyl, thienyl, imidazolinyl, pyridyl, etc.), and the like. Besides, these groups may have one or more substituents, such as hydroxy group, a lower alkyl group, an amino-lower alkyl group, a lower alkoxy group, amino group, a lower alkylamino group, mercapto group, a lower alkylthio group, amidino group, guanidino group, carbamoyl group, thiocarbamoyl group, sulfamoyl group, carbamoyloxy group, cyano group, carboxyl group, a lower alkoxycarbonyl group, a lower alkanoyloxy group, an aralkyloxycarbonyl group, oxo group, thioxo group, a halogeno group, a cycloalkyl group, an aryl group (e.g. phenyl, etc.), a heterocyclic group (e.g. pyrrolidinyl, piperidyl, furyl, thienyl, imidazolinyl, pyridyl, etc.), and the like.

The organic groups for $R^1$ or $R^2$ may optionally be protected by a protecting group, and the protecting group may be any conventional protecting groups.

The protecting groups for hydroxy group represented by $R^4$ are, for example, a lower alkoxycarbonyl group, a halogeno-lower alkoxycarbonyl group, a substituted or unsubstituted phenyl-lower alkyl group (e.g. benzyl group optionally being substituted by a nitro group or a lower alkoxy group), a tri-lower alkylsilyl group, a tri(substituted or unsubstituted phenyl)silyl group, a substituted or unsubstituted phenyl-lower alkoxycarbonyl group (e.g. benzyloxycarbonyl group optionally being substituted by a nitro group or a lower alkoxy group), and the like.

Throughout the present disclosure and claims, the lower alkyl group, the lower alkoxy group and the lower alkanol are ones having 1 to 6 carbon atoms, preferably 1 to 4 carbon atoms, respectively. The lower alkanoyl group is ones having 2 to 7 carbon atoms, preferably 2 to 5 carbon atoms, and the cycloalkyl group is ones having 3 to 8 carbon atoms, preferably 3 to 6 carbon atoms. The lower alkanate is ones wherein the lower alkanoyl moiety is alkanoyl groups having 2 to 7 carbon atoms, preferably 2 to 5 carbon atoms.

EXAMPLES

The present invention is illustrated in more detail by the following Examples and Reference Example, but should not be construed to be limited thereto.

Example 1

A mixture of sodium hydrogen carbonate (0.84 g) in water (10 ml), dimedone (0.84 g) and tetrahydrofuran (80 ml) is treated with ultrasonics, and thereto is added palladium diacetate (0.11 g) and triethyl phosphite (0.58 g) under nitrogen atmosphere, and the mixture is stirred for three minutes. To the mixture is added (1R,5S,6S)-2-[(4R)-pyrrolidine-2-thion-4-ylthio]-6-[(1R)-1-hydroxyethyl]-1-methylcarbapen-2-em-3-carboxylic acid allyl ester (3.83 g), and the mixture is stirred at 35°–37° C. for 45 minutes. The mixture is stirred at 5° C. for 30 minutes, and the precipitated crystals are collected by filtration, washed with tetrahydrofuran, and dried under reduced pressure to give (1R,5S,6S)-2-[(4R)-pyrrolidine-2-thion-4-ylthio]-6-[(1R)-1-hydroxyethyl]-1-methyl-carbapen-2-em-3-carboxylic acid sodium salt (3.28 g).

Yield: 90%

NMR (D₂O) δ: 1.22 (3H, d, J=7 Hz), 1.31 (3H, d, J=6 Hz), 2.87–3.07 (1H, m), 3.20–3.60 (3H, m), 3.55–3.72 (1H, m), 4.05–4.35 (4H, m)

Example 2

(1R,5S,6S)-2-[(4R)-Pyrrolidine-2-thion-4-ylthio)-6-[(1R)-1-hydroxyethyl]-1-methylcarbapen-2-em-3-carboxylic acid allyl ester (400 mg) is dissolved in tetrahydrofuran (16 ml), and thereto are added a solution of potassium hydrogen carbonate (105 mg) in water (4 ml) and dimedone (660 mg), and then further added thereto tetrakis(triphenylphosphine)palladium (0) (42 mg) under nitrogen atmosphere, and the mixture is stirred at 25° C. in the dark for 30 minutes. After the reaction is completed, the mixture is evaporated under reduced pressure to remove the solvent, and to the residue is added water (15 ml), and the mixture is washed with methylene chloride.

To the aqueous layer is added active charcoal (40 mg), and the mixture is filtered on celite (2 g). The residue is washed, and the washing and the aqueous layer are combined, and washed twice with chloroform. The resulting aqueous solution is concentrated under reduced pressure to remove the dissolved organic solvent, and subjected to lyophilization to give (1R,5S,6S)-2-[(4R)-pyrrolidine-2-thion-4-ylthio)-6-[(1R)-1-hydroxyethyl]-1-methylcarbapen-2-em-3-carboxylic acid potassium salt (328 mg).

Yield: 82%

NMR (D₂O) δ: 1.20 (3H, d), 1.29 (3H, d), 2.94 (1H, dd), 3.28–3.67 (4H, m), 4.06–4.27 (4H, m)

Example 3

To a solution of sodium hydrogen carbonate (84 mg) in water (1 ml) is added dimedone (84 mg), and the mixture is dissolved by treating with ultrasonics. Thereto is added ethanol (8 ml), and further treated with ultrasonics for five minutes. To the mixture are added palladium diacetate (11 mg), triethyl phosphite (0.06 ml) and (1R,5S,6S)-2-[(4R)-pyrrolidine-2-thion-4-ylthio)-6-[(1R)-1-hydroxyethyl]-1-methylcarbapen-2-em-3-carboxylic acid allyl ester (383 mg) under nitrogen atmosphere, and the mixture is stirred at 35°–38° C. for one hour, and stirred at 20° C. for 10 minutes, and then stirred at 5° C. for 20 minutes. The precipitated crystals are collected by filtration to give (1R,5S,6S)-2-[(4R)-pyrrolidine-2-thion-4-ylthio)-6-[(1R)-1-hydroxyethyl]-1-methylcarbapen-2-em-3-carboxylic acid sodium salt (157 mg). The mother liquor is concentrated under reduced pressure to remove the ethanol, and thereto is added water (20 ml). The mixture is washed five times with chloroform (20 ml), and the aqueous layer is subjected to lyophilization to give the above sodium salt (168 mg).

The NMR data of this product are the same as those of the product obtained in Example 1.

Example 4

Dimedone (169 mg) is dissolved in a solution of sodium hydrogen carbonate (169 mg) in water (2 ml) by ultrasonic treatment, and thereto are added dioxane (16 ml), palladium diacetate (23 mg) and triethyl phosphite (0.12 ml) under nitrogen atmosphere, and further added thereto (1R,5S,6S)-2-[(4R)-pyrrolidine-2-thion-4-ylthio]-6-[(1R)-1-t-butyldimethylsilyloxyethyl]-1-methylcarbapen-2-em-3-carboxylic acid allyl ester (1.03 g). The mixture is stirred at 30° C. for 30 minutes, and thereto is added diethyl ether (32 ml), and the mixture is stirred at 25° C. for 15 minutes, and further stirred at 5° C. for 30 minutes. The precipitated crystals are collected by filtration, washed with diethyl ether, and dried under reduced pressure at 25° C. for 17 hours to give (1R,5S,6S)-2-[(4R)-pyrrolidine-2-thion-4-ylthio]-6-[(1R)-1-t-butyldimethylsilyloxyethyl]-1-methylcarbapen-2-em-3-carboxylic acid sodium salt (885 mg).

M.p. 133°–136° C. (decomposed)

Examples 5–8

The compounds listed in Table 1 are treated in the same manner as in Examples 1–4 to remove a substituted or unsubstituted allyl group (—CH₂CH=CHR⁰) to give the corresponding de-allylated compounds.

TABLE 1

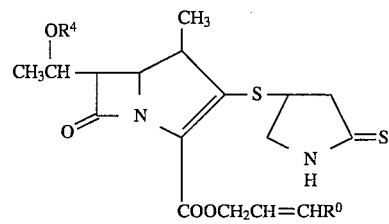

| Ex. No. | R⁴ | R⁰ |
| --- | --- | --- |
| 5 | Hydrogen atom | Methyl group |
| 6 | Hydrogen atom | Phenyl group |
| 7 | t-Butyldimethylsilyl group | Methyl group |
| 8 | t-Butyldimethylsilyl group | Phenyl group |

Examples 9–19

The compounds listed in Table 2 are treated in the same manner as in Examples 1–4 to remove an allyl group to give the corresponding de-allylated compounds.

TABLE 2

$$R^1 \underset{O}{\overset{X}{\underset{\displaystyle N}{\bigsqcup}}} \underset{COOCH_2-CH=CH_2}{\overset{\displaystyle \diagup}{\diagdown}} Y-R^2$$

| Ex. No. | R¹ | X | Y | R² |
|---|---|---|---|---|
| 9 | CH₃CH(OH)— | —CH(CH₃)— | Single bond | —⟨phenyl⟩—CH₂NH₂ |
| 10 | CH₃CH(OH)— | —CH(CH₃)— | Single bond | —⟨cyclopropyl⟩—NH₂ |
| 11 | CH₃CH(OH)— | —CH(CH₃)— | Single bond | —CH₂—⟨pyridyl-N⟩ |
| 12 | CH₃CH(OH)— | —CH₂— | S | —CH₂CH₂NH₂ |
| 13 | CH₃CH(OH)— | —S— | S | —CH₂CH₂OH |
| 14 | CH₃CH(OH)— | —O— | S | —CH₂CH₂NH₂ |
| 15 | CH₃CH(OH)— | —CH₂CH₂— | S | —CH₂CH₂NH₂ |
| 16 | ⟨thienyl-S⟩—CH₂CONH— | —S—CH₂— | Single bond | —CH₂OCOCH₃ |
| 17 | ⟨phenyl⟩—CH(NH₂)—CONH— | —S—CH₂— | Single bond | —CH₃ |
| 18 | HOOCCH(NH₂)—(CH₂)₃CONH— | —S—CH₂— | Single bond | —CH₂OCOCH₃ |
| 19 | CH₃CH₂— | —CH₂— | S | —CH₂CH₂NHCOCH₃ |

Reference Example 1

(1) To a mixture of (3S,4S)-3-[(1R)-1-t-butyldimethylsilyloxyethyl]-4-[(1R)-1-carboxyethyl]-2-azetidinone (10 g) and acetonitrile (50 ml) are added 4-dimethylaminopyridine (400 mg), t-butylmercaptane (5.98 g) and 1,3-dicyclohexylcarbodimide (8.22 g) at −5° C. The mixture is stirred at room temperature for 17 hours, and the insoluble materials are removed by filtration, and the filtrate is concentrated under reduced pressure. To the residue is added ethyl acetate, and the mixture is washed, dried and concentrated under reduced pressure. The residue is purified by silica gel column chromatography to give (3S,4S)-3-[(1R)-1-t-butyldimethylsilyloxyethyl]-4-[(1R)-1-t-butylthiocarbonylethyl]-2-azetidinone (11.7 g).

(2) To a mixture of the above compound (320 mg), bromoacetic acid allyl ester (169 mg) and tetrahydrofuran (1 ml) is added dropwise a 1M solution of sodium bis(trimethylsilyl)amide (0.94 ml) in tetrahydrofuran at −65° C. to −60° C., and the mixture is warmed to −30° C. The reaction solution is poured into water, and extracted with diethyl ether. The extract is washed, dried, and concentrated under reduced pressure. The residue is purified by silica gel column chromatography to give (3S,4S)-3-[(1R)-1-t-butyldimethylsilyloxyethyl]-4-[(1R )-1-t-butylthiocarbonylethyl]-1-(allyloxycarbonylmethyl)-2-azetidinone (538 mg).

(3) To a mixture of the above product (1 g) and tetrahydrofuran (6 ml) is added a 1M solution of sodium bis(trimethylsilyl)amide (4.24 ml) in tetrahydrofuran at −40° C. to −30° C. The mixture is stirred at −30° C. for five minutes, and thereto is added trimethylchlorosilane (230 mg) at −60° C. The mixture is stirred for five minutes, and thereto is added diphenylphosphoryl chloride (598 mg). The mixture is stirred at 0° C. for one hour, and the reaction solution is poured into a phosphate buffer (pH 7.0), and extracted with ethyl acetate. The extract is washed, dried, and concentrated under reduced pressure. The resulting residue is purified by reversed phase robber column (RP-8, manufactured by E. Merck) (solvent; acetonitrile:water=3:1) to give (1R,5R,6S)-6-[(1R)-1-t-butyldimethylsilyloxyethyl]-1-methyl-2-diphenylphosphoryloxycarbapen-2-em-3-carboxylic acid allyl ester (1.1 g) as oil.

(4) To a mixture of the above product (100 mg) and acetonitrile (0.5 ml) are added (4R)-4-mercaptopyrrolidine-2-thion (22 mg) and diisopropylethylamine (21 mg) at 0° C. The mixture is stirred at 0° C. for one hour, and poured into a phosphate buffer (pH 7.0), and extracted with ethyl acetate. The extract is washed, dried, and concentrated under reduced pressure, and the residue is purified by silica gel column chromatography (solvent; n-hexane:chloroform:ethyl acetate=5:5:4) to give (1R,5S,6S)-2-[(4R)-pyrrolidine-2-thion-4-ylthio]-6-[(1R)-1-t-butyldimethylsilyloxyethyl]-1-methylcarbapen-2-em-3-carboxylic acid allyl ester (57 mg).

(5) To a mixture of the above product (50 mg), tetrahydrofuran (0.5 ml) and acetic acid (6.0 mg) is added a 1M solution of tetra-n-butylammonium fluoride in tetrahydrofuran (0.35 ml) under ice-cooling, and the mixture is stirred at room temperature for two hours. To the reaction solution is added ethyl acetate, and the mixture is washed, dried, and concentrated under reduced pressure. The residue is purified by silica gel column chromatography (solvent; chloroform:ethanol=20:1) to give (1R,5S,6S )-2-[(4R )-pyrrolidine-2-thion-4-ylthio]-6-[(1R )-1-hydroxyethyl]-1-methylcarbapen-2-em-3-carboxylic acid allyl ester (13 mg).

M.p. 139°–141° C.

Effects of the Invention

According to the present invention, substituted or unsubstituted allyl groups are effectively removed under moderate conditions from a compound having substituted or unsubstituted allyl group-protecting carboxyl group, even though said compound has an unstable structure such as β-lactam compound, so that the desired compound can be obtained easily and in high yield without decomposition of the desired compound. Accordingly, the method of the present invention is industrially useful as a method for removing a substituted or unsubstituted allyl group from a carboxyl group.

What is claimed is:

1. A method for removing the the protecting group of the carboxyl group from a compound of the formula II:

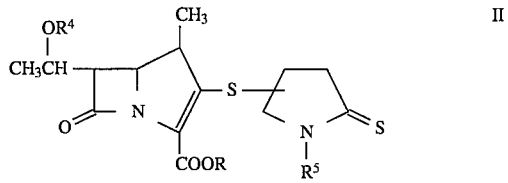

wherein R is the formula: —CH$_2$—CH=CHR$^0$, R$^0$ is a hydrogen atom, a lower alkyl group or a phenyl group, R$^4$ is a hydrogen atom or a protecting group for a hydroxy group, and R$^5$ is a hydrogen atom or a lower alkyl group comprising:

reacting said compound II with an alkyl-scavenger selected from the group consisting of dimedone, 1,3-cyclohexadione, acetylacetone, ethylacetoacetate, an N-lower alkyl aniline and aniline in the presence of a palladium (II) compound and a compound selected from the group consisting of a tri-lower alkyl phosphate and a triphenyl phosphine in an aqueous organic solvent.

2. The method according to claims 1, wherein R$^4$ is a hydrogen atom, a lower alkoxycarbonyl group, a halogeno-lower alkoxycarbonyl group, a phenyl-lower alkyl group, a phenyl lower alkyl group in which the phenyl group is substituted by a member selected from the group consisting of a nitro group and a lower alkoxy group, a tri-lower alkylsilyl group, a triphenylsilyl group, and a phenyl-lower alkoxycarbonyl group or a phenyl-lower alkoxycarbonyl group in which the phenyl group is substituted by a member selected from the group consisting of a nitro group and a lower alkoxy group.

3. The method according to claim 1, wherein R$^4$ is a hydrogen atom or a t-butyldimethylsilyl group, and R$^5$ is a hydrogen atom.

4. The method according to claim 1, wherein the palladium compound is a palladium (II) di-lower alkanate or a palladium dihalide.

5. The method according to claim 4, wherein the reaction is carried out in the presence of an alkali metal hydrogen carbonate, an alkali metal carbonate, an alkali metal hydroxide, an alkali metal hydride or an organic amine.

6. The method according to claim 1, wherein the palladium compound is a palladium (II) di-lower alkanate.

7. The method according to claim 1, wherein the compound selected from the group consisting of a tri-lower alkyl phosphite and a triphenylphosphine is a tri-lower alkyl phosphite.

8. The method according to claim 1, wherein the palladium compound is a palladium (II) di-lower alkanate and the compound selected from the group consisting of a tri-lower alkyl phosphite and a triphenylphosphine is a tri-lower alkyl phosphite.

9. The method according to claim 1, wherein the palladium compound is palladium (II) diacetate and the compound selected from the group consisting of a tri-lower alkyl phosphite and a triphenylphosphine is triethyl phosphite.

10. The method according to claim 1, wherein the aqueous organic solvent is a mixture of water and a polar organic solvent or a mixture of water and polar organic solvents, said organic solvent being selected from the group consisting of a lower alkanol, tetrahydrofuran, dioxane, dimethylformamide, dimethylsulfoxide, acetonitrile, acetone, and hexamethylphosphoric thiamide.

11. The method according to claim 10, wherein the polar organic solvent is selected from the group consisting of ethanol, tetrahydrofuran and dioxane.

12. The method according to claim 10, wherein the reaction is carried out in the presence of an alkali metal hydrogen carbonate, an alkali metal carbonate, an alkali metal hydroxide, an alkali metal hydride or an organic amine.

13. The method according to claim 1, wherein the allyl-scavenger is dimedone.

14. The method according to claim 13, wherein the reaction is carried out in the presence of an alkali metal hydrogen carbonate, an alkali metal carbonate, an alkali metal hydroxide, an alkali metal hydride or an organic amine.

15. The method according to claim 1, wherein the palladium compound is palladium (II) diacetate, the compound selected from the group consisting of a tri-lower alkyl phosphite and a triphenylphosphine is triethyl phosphite, the aqueous organic solvent is a mixture of water and a polar organic solvent which is selected from the group consisting of ethanol, tetrahydrofuran and dioxane, and the allyl-scavenger is dimedone.

16. The method according to claim 1, wherein the reaction is carried out in the presence of an alkali metal hydrogen carbonate, an alkali metal carbonate, an alkali metal hydroxide, an alkali metal hydride or an organic amine.

* * * * *